United States Patent
Wu et al.

(10) Patent No.: US 11,847,839 B2
(45) Date of Patent: Dec. 19, 2023

(54) DETECTING ANOMALOUS BEHAVIORS WITHIN AIRCRAFT CONTEXT

(71) Applicant: Rockwell Collins, Inc., Cedar Rapids, IA (US)

(72) Inventors: Peggy Wu, Ellicott City, MD (US); Arjun Harsha Rao, Marion, IA (US); Christopher L George, Winchester, VA (US); Timothy J. Wittkop, Marion, IA (US); Michael P. Matessa, Ben Lomond, CA (US); Wade T. Johnson, Cedar Rapids, IA (US)

(73) Assignee: Rockwell Collins, Inc., Cedar Rapids, IA (US)

(*) Notice: Subject to any disclaimer, the term of this patent is extended or adjusted under 35 U.S.C. 154(b) by 0 days.

(21) Appl. No.: 17/744,385

(22) Filed: May 13, 2022

(65) Prior Publication Data
US 2022/0392237 A1 Dec. 8, 2022

Related U.S. Application Data

(60) Provisional application No. 63/196,942, filed on Jun. 4, 2021.

(51) Int. Cl.
| | |
|---|---|
| G06V 20/59 | (2022.01) |
| G06V 40/16 | (2022.01) |
| G06V 40/20 | (2022.01) |
| G06V 10/764 | (2022.01) |
| G08G 5/04 | (2006.01) |
| A61B 5/318 | (2021.01) |

(Continued)

(52) U.S. Cl.
CPC ............ *G06V 20/59* (2022.01); *A61B 5/024* (2013.01); *A61B 5/318* (2021.01); *A61B 5/6888* (2013.01); *G06V 10/20* (2022.01); *G06V 10/764* (2022.01); *G06V 10/774* (2022.01); *G06V 40/174* (2022.01); *G08G 5/045* (2013.01)

(58) Field of Classification Search
CPC ............................. G06V 20/59; G06V 40/174
See application file for complete search history.

(56) References Cited

U.S. PATENT DOCUMENTS

| | | | |
|---|---|---|---|
| 9,613,543 B2 * | 4/2017 | Whitlow | B64D 45/0059 |
| 10,357,195 B2 | 7/2019 | Beck et al. | |

(Continued)

FOREIGN PATENT DOCUMENTS

| | | |
|---|---|---|
| EP | 2434465 A3 | 11/2012 |
| GB | 2564864 A | 1/2019 |

OTHER PUBLICATIONS

Extended Search Report in European Application No. 22176709.8 dated Oct. 12, 2022, 8 pages.

*Primary Examiner* — Rowina J Cattungal
(74) *Attorney, Agent, or Firm* — Suiter Swantz pc llo

(57) ABSTRACT

A pilot may be more stressed during take-off or landing, which is not abnormal. Physiological data of the pilot may be received. Placing the physiological data in context of the current situation may be advantageous in detecting anomalous behaviors of the pilot. A system and method are described. The system and method receive a stream of images from a camera and detect whether the pilot is exhibiting anomalous behavior. The anomalous behavior is further put into context based on the flight state and various avionics information.

11 Claims, 4 Drawing Sheets

(51) Int. Cl.
    *G06V 10/20*         (2022.01)
    *G06V 10/774*      (2022.01)
    *A61B 5/024*       (2006.01)
    *A61B 5/00*         (2006.01)

(56) References Cited

U.S. PATENT DOCUMENTS

| | | |
|---|---|---|
| 10,426,393 B2 | 10/2019 | Bosworth et al. |
| 2006/0011399 A1 | 1/2006 | Brockway et al. |
| 2006/0220883 A1* | 10/2006 | Matos ............... A62B 99/00 |
| | | 340/945 |
| 2012/0212353 A1* | 8/2012 | Fung ............... B60W 10/18 |
| | | 701/1 |
| 2016/0009411 A1 | 1/2016 | Davalos et al. |
| 2020/0000390 A1 | 1/2020 | Vollard-Derme et al. |
| 2020/0242343 A1 | 7/2020 | Schwindt et al. |
| 2020/0322527 A1 | 10/2020 | Orikasa et al. |
| 2021/0034053 A1 | 2/2021 | Nikolic et al. |
| 2021/0118078 A1 | 4/2021 | Wang et al. |

\* cited by examiner

DETECTING ANOMALOUS BEHAVIORS WITHIN AIRCRAFT CONTEXT

CROSS-REFERENCE TO RELATED APPLICATIONS

The present application claims the benefit under 35 U.S.C. Section 119(e) of U.S. Provisional Application No. 63/196,942, filed Jun. 4, 2021, which is incorporated herein by reference in the entirety.

TECHNICAL FIELD

The present disclosure generally relates to methods and systems for anomalous detection and more particularly to classifying anomalous behavior of pilots in a flight context.

BACKGROUND

Anomalous flight behaviors from pilots are self-monitored or monitored by a fellow crew member. Furthermore, the anomalous flight behaviors are not analyzed in light of a flight context. Therefore, it would be advantageous to provide a device, system, and method that cures the shortcomings described above.

SUMMARY

A system is described, in accordance with one or more illustrative embodiments of the present disclosure. In one illustrative embodiment, the system includes a camera configured to capture a stream of images within a flight deck of an aircraft. In another illustrative embodiment a non-transitory memory maintaining program instructions. In another illustrative embodiment, the system includes one or more processors configured to execute the program instructions maintained on the memory. In another illustrative embodiment, the program instructions cause the one or more processors to receive the stream of images and at least one of avionics information of the aircraft or a flight state of the aircraft. In another illustrative embodiment, the program instructions cause the one or more processors to determine at least one of a facial expression or a pose of a pilot within the flight deck based on the stream of images. In another illustrative embodiment, the program instructions cause the one or more processors to classify a behavior of the pilot based on at least one of the facial expression or the pose and classify a current flight context for the aircraft based on at least one of the avionics information or the flight state. In another illustrative embodiment, the program instructions cause the one or more processors to determine a probability distribution for the behavior of the pilot, wherein the probability distribution indicates the behavior is anomalous. In another illustrative embodiment, the program instructions cause the one or more processors to map the probability distribution for the behavior of the pilot to the current flight context to determine a pilot state. In another illustrative embodiment, the program instructions cause the one or more processors to provide the pilot state to a pilot monitoring system for alerting the pilot.

A method is disclosed, in accordance with one or more illustrative embodiments of the present disclosure. In one illustrative embodiment, the method includes receiving a stream of images and at least one of avionics information of the aircraft or a flight state of an aircraft. In another illustrative embodiment, the stream of images is received from a camera capturing the stream of images within a flight deck of the aircraft. In another illustrative embodiment, the method includes determining at least one of a facial expression or a pose of a pilot within the flight deck based on the stream of images. In another illustrative embodiment, the method includes classifying a behavior of the pilot based on at least one of the facial expression or the pose and classifying a current flight context for the aircraft based on at least one of the avionics information or the flight state. In another illustrative embodiment, the method includes determining a probability distribution for the behavior of the pilot, wherein the probability distribution indicates the behavior is anomalous. In another illustrative embodiment, the method includes mapping the probability distribution for the behavior of the pilot to the current flight context to determine a pilot state. In another illustrative embodiment, the method includes providing the pilot state to a pilot monitoring system for alerting the pilot.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

Implementations of the concepts disclosed herein may be better understood when consideration is given to the following detailed description thereof. Such description refers to the included drawings, which are not necessarily to scale, and in which some features may be exaggerated, and some features may be omitted or may be represented schematically in the interest of clarity. Like reference numerals in the drawings may represent and refer to the same or similar element, feature, or function. In the drawings.

DETAILED DESCRIPTION OF THE INVENTION

Figure 1A:
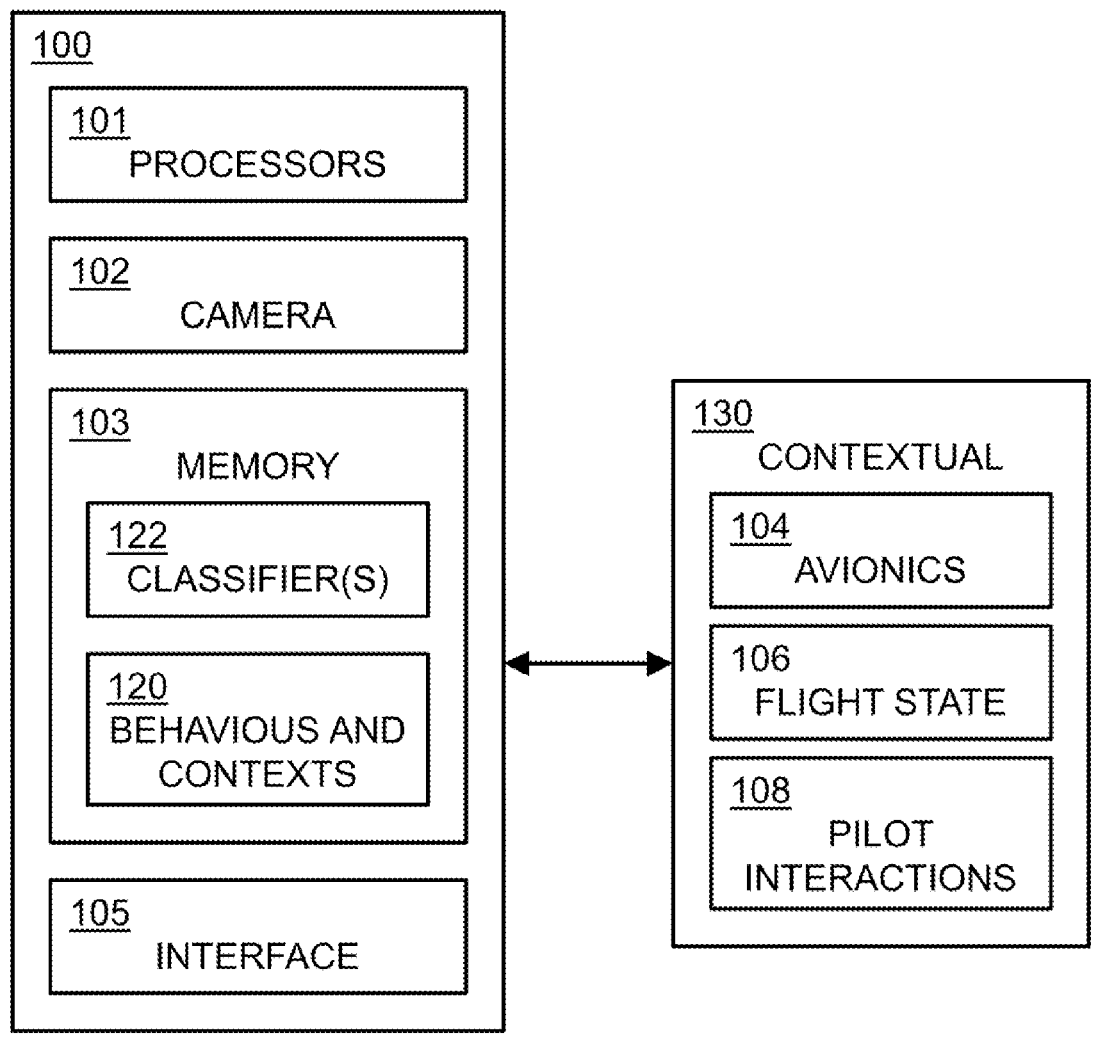
FIG. 1A depicts a simplified schematic diagram of a system, in accordance with one or more embodiments of the present disclosure.

Before explaining one or more embodiments of the disclosure in detail, it is to be understood that the embodiments are not limited in their application to the details of construction and the arrangement of the components or steps or methodologies set forth in the following description or illustrated in the drawings. In the following detailed description of embodiments, numerous specific details may be set forth in order to provide a more thorough understanding of the disclosure. However, it will be apparent to one of ordinary skill in the art having the benefit of the instant disclosure that the embodiments disclosed herein may be practiced without some of these specific details. In other instances, well-known features may not be described in detail to avoid unnecessarily complicating the instant disclosure.

As used herein a letter following a reference numeral is intended to reference an embodiment of the feature or element that may be similar, but not necessarily identical, to a previously described element or feature bearing the same reference numeral (e.g., 1, 1a, 1b). Such shorthand notations are used for purposes of convenience only and should not be construed to limit the disclosure in any way unless expressly stated to the contrary.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" may be employed to describe elements and components of embodiments disclosed herein. This is done merely for convenience and "a" and "an" are intended to include "one" or "at least one," and the singular also includes the plural unless it is obvious that it is meant otherwise.

Finally, as used herein any reference to "one embodiment" or "some embodiments" means that a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination or sub-combination of two or more such features, along with any other features which may not necessarily be expressly described or inherently present in the instant disclosure.

Reference will now be made in detail to the subject matter disclosed, which is illustrated in the accompanying drawings. Broadly embodiments of the present disclosure are directed to systems and methods for detecting anomalous flight behaviors. An approach to monitoring anomalous behaviors is described, in accordance with one or more embodiments of the present disclosure. The behavior of a pilot may be monitored by one or more cameras. The behavior may be classified based on one or more of a facial expression, a pose, or an interaction with the aircraft detected in the images captured by the camera. The behaviors may be monitored and then compared with one or more operational contexts of the aircraft. Such operational contexts may be determined based on avionics information, flight state, or pilot interactions. Deviations from expected norms may be monitored to tag the pilot behavior as an anomalous event within an associated time frame. Based on the monitored anomalous events, a time series profile of patterns of behavior may be developed. Repeated patterns of anomalous behavior may indicate various contributing factors, such as, but not limited to, pilot impaired performance, lack of competency, or malicious behaviors. Thus, such anomalous behaviors may be detected from the time variant information. An objective evaluation of pilot behavior over the entire duration of flight may then be developed within the context of the phases of flight. Context from various sources may be leveraged to reduce potential false alarms and provide deeper insight of the pilot state during anomalous behaviors.

Figure 1B:
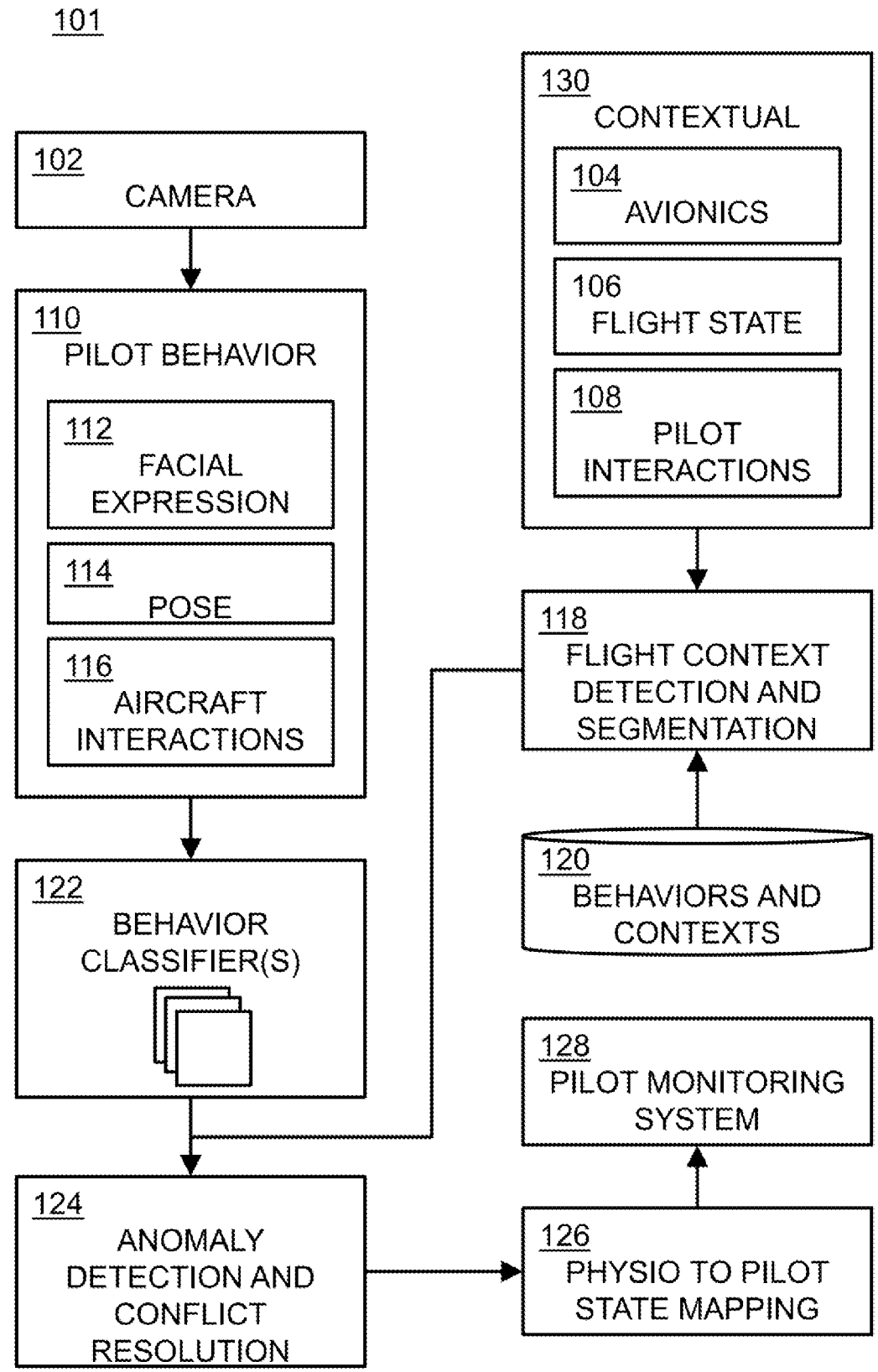
FIG. 1B depicts one or more processing streams of a processor, in accordance with one or more embodiments of the present disclosure.

Referring generally to FIGS. 1A-1C, a system 100 to detect an anomalous behavior of a pilot is described, in accordance with one or more embodiments of the present disclosure. The system 100 may be utilized in a flight deck of an aircraft. The system 100 may be provided to determine anomalous behavior of an operator within the flight deck. The system 100 may detect whether the behavior of the operator within the flight deck is in accordance with normal behavior for the given context or if the behaviors is abnormal, and subsequently provide an alert to the operator.

Referring now to FIG. 1A, a simplified schematic diagram of the system 100 is described. The system 100 may include one or more processors 101, a camera 102, a memory 103, and a network interface 105. The processor 101 may generally be configured to receive various information and execute one or more program instructions for detecting whether the behavior of the user within the flight deck is abnormal. For instance, the processor 101 may receive a stream of images from the camera 102. The processor 101 may further receive various other information from the network interface 105, such as, contextual information 130 including avionics information 104, flight state 106 information, and pilot interactions 108. In embodiments, the system 100 may include the processor 101 and the memory 103. The memory 103 may maintain program instructions which may be executed by the processor. By executing the program instructions, the processor 101 may execute any of the various process steps described throughout the present disclosure, such as detection abnormal behavior.

For the purposes of the present disclosure, the term processor 101 or "processing element" may be broadly defined to encompass any device having one or more processing or logic elements (e.g., one or more microprocessor devices, one or more application specific integrated circuit (ASIC) devices, one or more field programmable gate arrays (FPGAs), one or more digital signal processors (DSPs)), a special purpose logic device (e.g., ASICs)), or other integrated formats. In this sense, the one or more processors may include any device configured to execute algorithms and/or instructions (e.g., program instructions stored in memory). Those skilled in the art will recognize that aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software/and or firmware would be well within the skill of one skilled in the art in light of this disclosure. Such hardware, software, and/or firmware implementation may be a design choice based on various cost, efficiency, or other metrics. In this sense, the processor(s) may include any microprocessor-type device configured to execute software algorithms and/or instructions. In general, the term "processor" may be broadly defined to encompass any device having one or more processing elements, which execute program instructions from memory, from firmware, or by hardware implemented functions. It should be recognized that the steps described throughout the present disclosure, such as, but not limited to, the method described herein, may be carried out by the processors 101.

For the purposes of the present disclosure, the memory 103 may include any storage medium known in the art suitable for storing program instructions executable by the associated processor. For example, the memory medium may include a non-transitory memory medium. For instance, the non-transitory memory medium may include, but is not limited to, a read-only memory (ROM), a random-access memory (RAM), a magnetic or optical memory device (e.g., disk), a solid-state drive and the like. It is further noted that memory medium may be housed in a common controller housing with the processor. For example, the memory and the processor may be housed in a line replaceable unit, an integrated modular avionics (IMA) controller, or the like. In an alternative embodiment, the memory may be located remotely with respect to the physical location of the processor. In another embodiment, the memory maintains program instructions for causing the processor(s) to carry out the various steps described through the present disclosure.

In some embodiments, the processor 101 is configured to receive the information from a network interface 105. The network interface 105 may include any standard interface, such as, but not limited to, ARINC 429, ARINC-664, ethernet, AFDX, serial, CAN, TTP, Military Standard (MIL-STD) 1553, peripheral component interconnect (PCI) express, digital interfaces, analog interfaces, discrete interfaces, or the like. The network interface 105 may include any wireline communication protocol (e.g., DSL-based interconnection, cable-based interconnection, T9-based interconnection, and the like) or wireless communication protocol (e.g., GSM, GPRS, CDMA, EV-DO, EDGE, WiMAX, 3G, 4G, 4G LTE, 5G, Wi-Fi protocols, RF, Bluetooth, and the like) known in the art. By the network interface 105, the processor may be configured to receive information from one or more systems, such as, but not limited to, a camera, bioinformatic sensors, or an avionics system. During flight, the processors 101 may receive information (e.g., by way of the network interface 105). The processors 101 may receive the video stream from the camera 102. The processors 101 may then analyze the video stream to determine a fatigue level of the operator.

The camera 102 is described, in accordance with one or more embodiments. The camera 102 may include any suitable camera. For example, the camera 102 may include various mechanical or electrical components for capturing an image or an image stream associated with the pilot. The camera 102 may capture a stream of images of the user within the flight deck. The camera 102 may be communicatively coupled to the processors 101. For example, the camera 102 may be communicatively coupled to the processors 101 by way of the network interface 105. The camera 102 may thus provide the stream of images to the processors 101. The camera 102 may be disposed in a number of locations within the aircraft system 100, such as, but not limited to, within a head-mounted display or coupled to the flight deck of the cockpit. In embodiments, the stream of images captured by the camera 102 includes one or more of an eye of the user gazing at various locations within the flight deck, a facial expression of the user, a pose (e.g., a position and orientation) of the user, or an interaction of the user with the various instruments and displays within the flight deck. The camera 102 may be positioned and oriented to capture one or more of the eye, the facial expression, the gaze, or the aircraft interactions during operation of the aircraft.

In embodiments, the system 100 receives contextual information 130 associated with one or more of avionics information 104, flight state 106 information, and/or pilot interaction 108 information. The system 100 may receive the contextual information 130 by way of the network interface 105. The contextual information 130 may then be provided to the processors 101 for handling in one or more processing streams.

The system 100 may also be configured to receive avionics information 104 from one or more avionics systems. The avionics information 104 is now described in accordance with one or more embodiments of the present disclosure. The avionics information 104 may include any suitable avionics information, such as, but not limited to, attitude information, heading information, or traffic alert and collision avoidance (TCAS) information. The TCAS information may include a monitor of the aircraft in relation to other aircraft with a corresponding transponder or as indicated by air traffic control. The TCAS information may be received from a TCAS system, and the like.

The system 100 may also be configured to receive flight state 106 information from one or more avionics systems. The flight state 106 information is now described in accordance with one or more embodiments of the present disclosure. The flight state 106 may indicate a current flight state of the aircraft. The flight state 106 may include any flight state, such as, but not limited to, a take-off state, a taxi state, a cruise state, or a landing state. During a cruise state a pilot may be expected to look at instrumentation at a reduced level, as compared to during a take-off state or a landing state.

The system 100 may also be configured to receive pilot interaction 108 information from one or more pilot monitoring sensors. The pilot interaction 108 information is now described in accordance with one or more embodiments of the present disclosure. The pilot interaction 108 information may include any interaction regarding the pilot, such as, but not limited to, heart rate, an electrocardiogram (ECG), or the like. The heart rate and ECG may be collected by a sensor coupled to the user, such as by a chest strap, a wrist watch, a helmet, or the like.

Referring now to FIG. 1B, one or more processing streams of the processors 101 are described. The processors 101 may receive information from one or more sources. Such information may include, but is not limited to, information from the camera 102 or the contextual information 130 including one or more of the avionics information 104, flight state 106, or pilot interaction 108. The processors 101 may receive the information by way of one or more the network interfaces 105. The processors 101 may then use the stream of images from the camera 102 together with the contextual information 130 to determine whether a pilot behavior exhibited in the images is abnormal given the context of the aircraft.

In a first processing stream, the processors 101 may receive the stream of images from the camera 102. The processors 101 may then determine a pilot behavior 110 based on the stream of images from the camera 102. The pilot behavior 110 is now described, in accordance with one or more embodiments of the present disclosure. The pilot behavior 110 may include one or more of a facial expression 112, a pose 114, or an aircraft interaction 116. In this regard, the facial expression 112, the pose 114, and the aircraft interactions 116 may be determined, at least in part, from the camera 102. For example, the processor 101 may execute one or more classification algorithms to classify the facial expression of the pilot based on the images. By way of another example, the processors 101 may execute one or more classification algorithms to classify the pose (e.g., position and orientation) of the pilot based on the images. By way of another example, the processors 101 may execute one or more classification algorithms to determine how the pilot is interacting with the various user interface elements and displays of the aircraft. In some instances, the aircraft interactions 116 is based on the pose 114 together with various gaze information. The aircraft interactions 116 may include, but is not limited to, a scan pattern or a physical interaction of the pilot with one or more user interface elements. For example, the scan pattern may be analyzed to determine whether the focus of the pilot is fixed to a single indicator or screen or is otherwise spending too much time focused on the wrong screen or indicator when an alert has appeared on a different screen or indicator. By way of another example, the pilot may be repeatedly extending and retracting landing gears, which may be anomalous during cruise.

The pilot behavior, including one or more of the facial expressions 112, the pose 114, and the aircraft interactions 116, may then be provided to a behavior classifier 122 executed by the processors 101. The behavior classifier 122 is now described. The behavior classifier 122 may receive the pilot behavior 110. Based on such information, the behavior classifier 122 may classify the pilot behavior 110. The behavior may be classified based on a combination of time-variant changes in the camera 102 and one or more of the avionics 104, the flight state 106, or the pilot interactions 108. The behavior may then be bucketed into one or more buckets. Such buckets may provide information regarding whether the flight behavior is normal or abnormal. For example, physiological interactions of the pilot during take-off are expected to be significantly different than during cruise. During cruise a pilot's physiological interactions may be more relaxed. If the pilot's physiological interactions are similar to cruise while the pilot is currently in a take-off procedure, the system 100 may determine an anomaly is present.

In some instances, normal behavior (e.g., nominal behavior) and abnormal behavior may be pilot dependent. Pilots may typically exhibit idiosyncrasies. For example, pilots may exhibit idiosyncrasies within facial features, sitting positions, or the interactions with the aircraft. In this regard, the behavior classifier 122 may be trained for each pilot. In embodiments, the behavior classifier 122 may classify the pilot behavior 110 by an unsupervised learning process. The unsupervised learning process may include any unsupervised process of classification, such as, but not limited to, an unsupervised machine learning algorithm. Thus, such behavior classifier 122 may classify the pilot behavior 110 into one or more buckets (e.g., data bins) without a predefined thresholds determined by a supervised learning method. The use of the unsupervised learning process may be advantageous in allowing the processors 101 to retrain the behavior classifier for each pilot. It is further contemplated that the behavior classifier 122 may classify the pilot behavior 110 by a supervised learning process or any other classifier.

The processors 101 may also be configured to use multiple of the behavior classifiers 122. The use of multiple of the behavior classifiers may be advantageous in improving the redundancy of the classification of the pilot state.

In a second processing stream, the processors 101 may receive the contextual information 130, including one or more of the avionics information 104, the flight state 106, and the pilot interactions 108. The processors 101 may also receive behaviors and contexts 120 in the second processing stream. The behaviors and contexts 120 are now described, in accordance with one or more embodiments of the present disclosure. The behaviors and contexts 120 may provide heuristics of different behaviors that are known ahead of time. In this regard, the behaviors and contexts 120 may include previous behaviors and previous contexts associated with the previous behaviors. In some instances, the behaviors and contexts 120 may include behaviors and the contexts associated with the behaviors for the pilot. For example, the pilot behaviors may indicate the pilot was exhibiting normal behaviors for a given context of flight. The normal condition may generally indicate the pilot was performing according to expected pilot behavior. By way of another example, the pilot behaviors may indicate the pilot was exhibiting abnormal behaviors for a given context of flight. The abnormal condition may generally indicate the pilot was performing according to expected pilot behavior in the associated context. In some instances, the behaviors and contexts 120 may be generalized to other pilots, and is not associated with the pilot currently operating the aircraft.

The behaviors and contexts 120 may be maintained in a database on the memory 103. The memory 103 may maintain the behaviors and contexts 120 for a given time, such as, but not limited to, for a flight or in perpetuity. In some instances, the behaviors and contexts 120 are generated by the anomaly detection and conflict resolution 124 during flight and stored in the memory 103, although this is not intended to be limiting.

Flight context detection and segmentation 118 is not described, in accordance with one or more embodiments of the present disclosure. The processors 101 may receive one or more of the contextual information 130 and the behaviors and contexts 120. The processors 101 may then determine a flight context detection and segmentation 118 based on one or more of the contextual information 130 and the behaviors and contexts 120. The flight context detection and segmentation 118 may identify features that are relevant for certain buckets (e.g., a data bin). The behaviors and contexts 120 may be used by the flight context detection and segmentation 118 to learn what the actual flight segment is.

In some instances, the aircraft may be transitioned between a number of contexts. The one or more processors may use a context classifier to classify the context of the flight. In embodiments, the context classifier may classify the flight context by an unsupervised learning process. The unsupervised learning process may include any unsupervised process of classification. Thus, such the context classifier may classify the context into one or more buckets (e.g., data bins) without a predefined thresholds determined by a supervised learning method. It is further contemplated that the context classifier may classify the context of the flight by a supervised learning process or any other classifier. The use of the supervised learning method for the context classifier may be advantageous given that many flight contexts may be predetermined before flight.

An exemplary flight context is now described. For example, the aircraft may be in cruise and the avionics 104 of the aircraft may include a camera looking down at the terrain. The camera sensor may determine a pixel color or intensity below the aircraft. During an operational phase, the camera sensor may indicate the aircraft is flying above snow. During a subsequent operational phase, the camera sensor may indicate the aircraft is flying above sea. The processors 101 may receive the stream of images from the camera and use the stream of images in the flight detection and segmentation 118 to classify images into one or more buckets. The information based on the pixel information may be bucketed into a separate cluster or context. Determining whether the aircraft is over sea or snow may be advantageous for a subsequent processing when placing the pilot behavior in context with the flight context. By way of another example, the flight state 106 may indicate the aircraft is in a take-off, cruise, or landing procedure.

The processors 101 may then use the information determined from the behavior classifier 122 and the flight context detection and segmentation 118 for anomaly detection and conflict resolution 124. The anomaly detection and conflict resolution 124 is now described, in accordance with one or more embodiments of the present disclosure. The anomaly detection and conflict resolution 124 may occur based on one or more of the buckets determined by the behavior classifier 122. The anomaly detection and conflict resolution 124 may occur based on one or more of the buckets determined by the context classifier of the flight context detection and segmentation.

In some instances, multiple of the behavior classifiers 122 are used to classify the behavior of the pilot. Each of the behavior classifiers 122 may be provide more or less accurate classifications, which is dependent upon the flight context. Thus, the behavior classifiers 122 may output conflicting classifications. The conflict resolution of the anomaly detection and conflict resolution 124 may include resolving the conflicts between the behavior classifiers 122. The conflict resolution may resolve the conflict based on the flight context. For example, a first behavior classifier may indicate the pilot is making a face and a second behavior classifier may indicate the pilot is not making a face. When a detection is made that the pilot is making a face, the conflict resolution may determine whether the face is being made due to a change in the state of the pilot, as determined by the flight context detection and segmentation 118, or whether that is a normal face for the pilot. The conflict resolution may thus arbitrate between outputs from multiple classifiers. The conflict resolution may include determining the context of flight and selecting the output from one of the classifiers based on the context. For example, one algorithm may work well in one context and another algorithm may work well in a different context. The conflict resolution may look the context and then weight the results from the first algorithm higher than the second algorithm.

In some instances, the behavior classifier 122 may receive a stream of images, wherein one or more of the images exhibit a sensor error. The sensor error in the stream of images may cause the behavior classifier to incorrectly classify the behavior as abnormal. The anomaly detection of the anomaly detection and conflict resolution 124 may include detection anomalous sensor readings and remove the anomalous sensor readings as an outlier. For example, the anomaly detection may include determining whether the outliers are due to a sensor error or whether the outliers a valid issue due to a pilot behavior.

The anomaly detection and conflict resolution 124 may thus receive the flight context and the pilot behavior, put into bins of what is the probability distribution of this being a normal facial expression, an abnormal facial expression, or an outlier to be thrown out. The processor 101 then determines a probability distribution that the pilot state should fall under normal, anomaly, or sensor error.

The processors 101 may then use the probability distribution determined by the anomaly detection and conflict resolution 124 to perform a physiological to pilot state mapping 126. The physiological to pilot state mapping 126 is described, in accordance with one or more embodiments of the present disclosure. The processors 101 may be configured to map the physiological information to the pilot state. By mapping the physiological information to the pilot state, the processors may put the probability distribution within the flight context. For example, the pilot may be determined to be squinting. The physiological to pilot state mapping 126 may include determining the pilot is squinting as being a normal or abnormal based on the flight context. In this regard, the aircraft may be angled toward the sun, such that the flight context indicates a pilot may normally squint. The physiological to pilot state mapping 126 may be advantageous in providing outputs which are human interpretable. For example, the probability distributions from the anomaly detection and conflict resolution 124 may be difficult to decipher in-flight. The outputs from the physiological to pilot state mapping 126 may indicate a word, such as the pilot is fatigue, stressed, or the like.

The physiological information may include the various information from the pilot behavior, such as, but not limited to, facial expression 112, pose 114, or the aircraft interactions 116. The physiological information may also include various physiological information such as but not limited to Electroencephalograms (EEG), Electrocardiograph (ECG), pulse sensor, oxygen sensor, galvanic skin response (GSR), or any other biometric data sensing device. However, it is contemplated that where the system 100 is provided in commercial aviation, such information may be unavailable.

The processors 101 may then provide the mapped pilot state to a pilot monitoring system 128. In embodiments, the processors 101 may provide the mapped pilot state to a pilot monitoring system 128 in response to determining the behavior of the pilot is anomalous or abnormal. The pilot monitoring system 128 is now described, in accordance with one or more embodiments of the present disclosure. The pilot monitoring system 128 may provide an alert to the pilot in response to receiving the mapped state. The pilot monitoring system may also engage one or more procedures to ensure the safe operation of the aircraft. For example, the pilot monitoring system may engage an Automatic Ground Collision Avoidance System (Auto GCAS) may, when engaged, assume control of the aircraft as needed to avoid Controlled Flight into Terrain accidents. Such Auto GCAS may be implemented in variety of aircraft, such as, but not limited to, an F-35. The pilot monitoring system 128 may include any suitable pilot monitoring system, such as, but not limited to, an in-aircraft system, a co-pilot, or a ground control.

Figure 2:
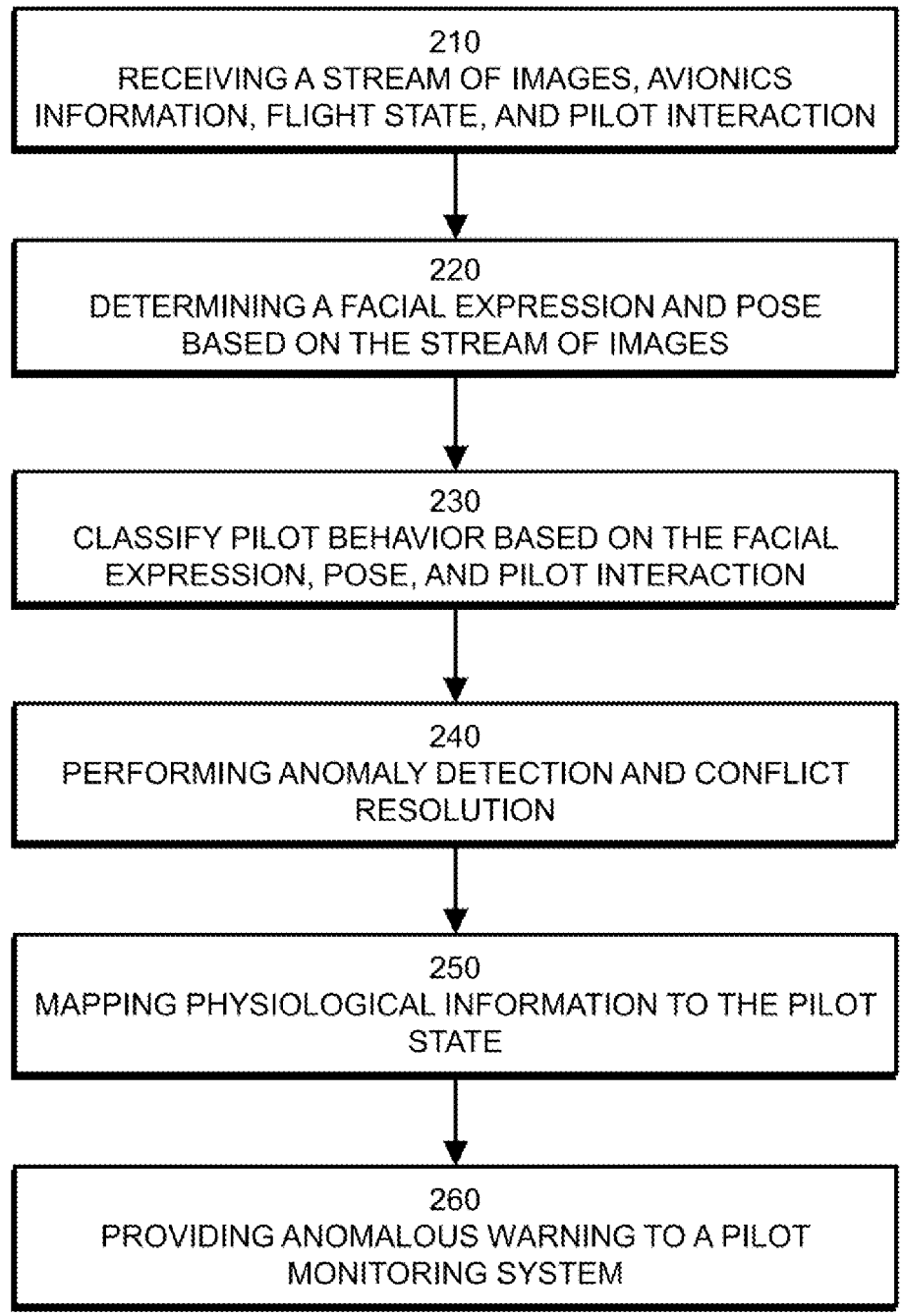
FIG. 2 depicts a flow-diagram of a method, in accordance with one or more embodiments of the present disclosure.

Referring now to FIG. 2, a method is described, in accordance with one or more embodiments of the present disclosure. The embodiments and the enabling technologies described previously herein in the context of the alerting system 100 should be interpreted to extend to the method 200. It is further recognized, however, that the method 200 is not limited to the alerting system 100.

In a step 210, information is received from a network. The information may include a stream of images associated with a pilot, avionics information, a flight state, or a pilot interaction with an aircraft.

In a step 220, one or more of a facial expression or a pose of the pilot is determined based on the stream of images associated with the pilot.

In a step 230, the pilot behavior is classified based on one or more of the facial expressions, the pose, or the pilot interaction. A current flight context for the aircraft may also be classified based on at least one of the avionics information or the flight state In a step 240, anomaly detection and conflict resolution may be performed. The anomaly detection and conflict resolution may include determining a probability distribution for the behavior of the pilot. The probability distribution may indicate the behavior is anomalous.

In a step 250, physiological information is mapped to the pilot state. The probability distribution for the behavior of the pilot may be mapped to the current flight context to determine a pilot state. The pilot state may be a human readable indicator, such as a stress level or a fatigue level.

In a step 260, an anomalous warning is provided to a pilot monitoring system. The pilot state is provided to the pilot monitoring system for alerting the pilot.

The method described herein may include storing results of one or more steps of the method embodiments in memory. The results may include any of the results described herein and may be stored in any manner known in the art. The memory may include any memory described herein or any other suitable storage medium known in the art. After the results have been stored, the results can be accessed in the memory and used by any of the method or system embodiments described herein, formatted for display to a user, used by another software module, method, or system, and the like. Furthermore, the results may be stored "permanently," "semi-permanently," temporarily," or for some period of time. For example, the memory may be random access memory (RAM), and the results may not necessarily persist indefinitely in the memory. It is further contemplated that each of the embodiments of the method described above may include any other step(s) of any other method(s) described herein. In addition, each of the embodiments of the method described above may be performed by any of the systems described herein. It is to be noted that the specific order of steps in the foregoing disclosed methods are examples of exemplary approaches. Based upon design preferences, it is understood that the specific order of steps in the method can be rearranged while remaining within the scope of the present disclosure.

Figure 3:
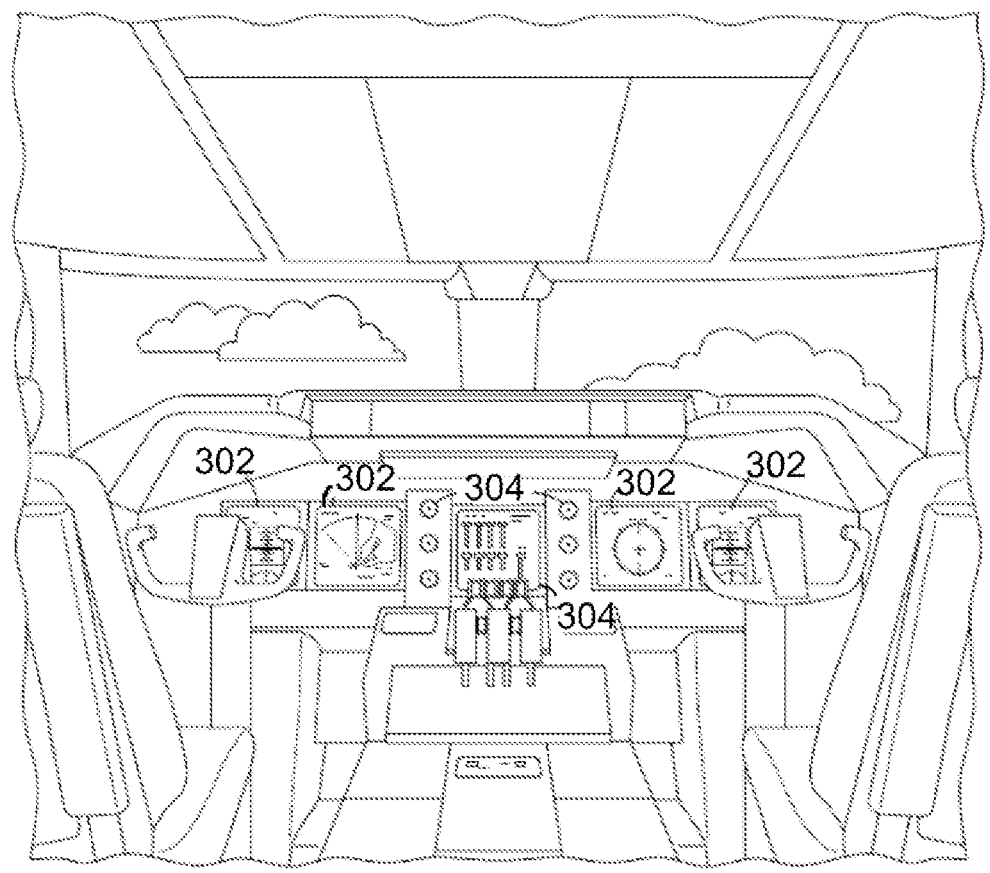
FIG. 3 depicts a perspective view of a flight deck of an aircraft, in accordance with one or more embodiments of the present disclosure.

Referring now to FIG. 3, a flight deck 300 of an aircraft is described, in accordance with one or more embodiments of the present disclosure. The system 100 may be embodied within the cockpit or flight deck 300. The system 100 may further include various components disposed outside of the flight deck 300, such as, but not limited to processing elements housed in a line replaceable unit (LRU), an integrated modular avionics (IMA) controller, or the like. The flight deck 300 may include an aircraft operator (not depicted), such as a pilot, a co-pilot, or a second officer seated within the cockpit. The flight deck 300 may also include one or more flight displays 302, aircraft instruments 304, and the like. The number and arrangement of the various elements within the flight deck 300 may be based on the type of the aircraft. Thus, the configuration of FIG. 3 is not intended to be limiting but is merely provided for exemplary purposes.

The flight deck 300 may include one or more flight displays 302. The flight displays 3 may be implemented using any of a variety of display technologies, including CRT, LCD, organic LED, dot matrix display, and others. The flight displays 302 may be configured to function to display various information known in the art. The flight displays 302 may be configured to function as one or more of a primary flight display (PFD) or a multifunction display (MFD). Such PFD and MFDs may be mounted in front of both a pilot and a copilot. The MFD may be mounted between the PFD of the pilot and the PFD of the copilot. Thus, the flight displays 302 may provide instrumentation for the operation of an aircraft. The flight displays 302 may be configured to function as, for example, a primary flight display (PFD) used to display altitude, airspeed, vertical speed, navigation and traffic collision avoidance system (TCAS) advisories; a crew alert system (CAS) configured to provide alerts to the flight crew; a multi-function display used to display navigation maps, weather radar, electronic charts, TCAS traffic, aircraft maintenance data and electronic checklists, manuals, and procedures; an engine indicating and crew-alerting system (EICAS) display used to display critical engine and system status data, and so on. Other types and functions of the flight displays are contemplated and will be apparent to those skilled in the art.

The flight deck 300 may include one or more aircraft instruments 304. The aircraft instruments 304 may include, but are not limited to, left, center, right, overhead, second officer, or other aircraft instruments. The aircraft instruments 304 may be implemented using any of a variety of technologies, including CRT, LCD, organic LED, dot matrix display, and others. It is further contemplated that the aircraft instruments 304 of the flight deck 300 may include aircraft instruments (panels) which use analog indicators. The aircraft instruments 304 may indicate information associated with various flight instruments of the aircraft, such as, but not limited to, attitude, heading, vertical speed, air speed, altimeter, or turn. The aircraft instruments 304 may also indicate information associated with various engine instruments of the aircraft, such as, but not limited to, fuel quantity, oil quantity, oil pressure, oil temperature, tachometer, temperature, braking pressure, braking temperature, among others. The aircraft instruments 304 may also indicate information associated with various navigation instruments of the aircraft. Other types and functions of the aircraft instruments 304 are contemplated and will be apparent to those skilled in the art.

An operator (e.g., pilot, co-pilot or other cockpit crewmember) may be seated in a cockpit or like control space throughout one or more flight states of the aircraft, such as, but not limited to, pre-flight checks, taxiing, flight segments (e.g., takeoff, climb, cruise, descent, landing), and taxiing to a final destination before disembarkation, apart from short periods when the operator may not be in control of the aircraft (e.g., when another pilot or operator takes control so the operator may temporarily leave the cockpit). While seated in the flight deck 300, the operator may interact with or otherwise visually engage with various components of the cockpit, such as the flight display 302 or the aircraft instruments. During flight operations, a face of the operator may exhibit various facial expressions. The operator may also exhibit various poses during flight operations. The operator may also interact with (e.g., gaze or physically interact with) various components of the flight deck 300. The facial expressions, the pose, and the aircraft interactions may provide a biomarker of the behavior for the aircraft operator. The biomarker may be indicative of a fatigue, a stress, or the like, of the operator.

In embodiments, the camera 102 may be disposed within the flight deck 300 and oriented toward the operator. The camera 102 may be disposed in any suitable location of the flight deck 300. For example, the camera 102 may be mounted to the flight deck 300, coupled to a head mounted display, or the like. The camera 102 may be oriented for capturing a stream of images of the operator. The image stream may then be analyzed to detect a facial expression, gaze, or body pose of the operator within the stream of images. For example, the stream of images may capture frames of images as the operator interacts with cockpit interfaces (e.g., as the operator guides the aircraft through taxi, takeoff, and initial climb, scanning cockpit displays and windows throughout), tracking changes in the operator's facial expression, gaze, and body pose.

Referring generally again to FIGS. 1A-3. The herein described system 100 illustrates different components contained within, or connected with, other components by the network. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected," or "coupled," to each other to achieve the desired functionality, and any two components capable of being so associated can also be viewed as being "couplable," to each other to achieve the desired functionality. Specific examples of couplable include but are not limited to wirelessly interactable and/or wirelessly interacting components and/or logically interacting and/or logically interactable components.

In example implementations, the concepts of the present disclosure may be incorporated in an aircraft. Using the concepts disclosed herein, flight anomalous behaviors may be detected. Although example embodiments of the present disclosure are shown and described in an aviation environment, the inventive concepts of the present disclosure may be configured to operate in any type of vehicle known in the art. In the interest of simplicity and to most clearly define the inventive concepts of the present disclosure, embodiments may be described throughout the present disclosure in an aircraft environment. However, these references are not to be regarded as limiting. Thus, references to "aircraft" or "aviation," and like terms should not be interpreted as a limitation on the present disclosure, unless noted otherwise herein.

One skilled in the art will recognize that the herein described components operations, devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components, operations, devices, and objects should not be taken as limiting.

It will be understood by those within the art that, in general, terms used herein, and especially in the appended claims are generally intended as "open" terms (e.g., the term "including" should be interpreted as "including but not limited to," the term "having" should be interpreted as "having at least," the term "includes" should be interpreted as "includes but is not limited to," and the like). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A system comprising:
   a camera configured to capture a stream of images within a flight deck of an aircraft;
   a non-transitory memory maintaining program instructions; and
   one or more processors configured to execute the program instructions maintained on the memory, the program instructions causing the one or more processors to:
      receive the stream of images and at least one of avionics information of the aircraft and a flight state of the aircraft, wherein the avionics information comprises a pixel color or intensity below the aircraft determined by a camera sensor, wherein during an operational phase the camera sensor indicates the aircraft is flying above one of sea or snow, wherein the flight state comprises cruise;
      determine at least one of a facial expression or a pose of a pilot within the flight deck based on the stream of images, wherein the pilot is determined to be squinting;
      classify a behavior of the pilot based on at least one of the facial expression or the pose and classify a current flight context for the aircraft based on at least one of the avionics information or the flight state, wherein the current flight context includes determining whether the aircraft is over sea or snow;
      determine a probability distribution for the behavior of the pilot, wherein the probability distribution indicates the behavior is anomalous;
      map the probability distribution for the behavior of the pilot to the current flight context to determine a pilot state, wherein the mapping includes determining the pilot is squinting as being normal or abnormal based on the current flight context; and
      provide the pilot state to a pilot monitoring system for alerting the pilot;
   wherein the one or more processors are configured to use at least two behavior classifiers for classifying the behavior of the pilot; wherein determining the probability distribution for the behavior further includes performing conflict resolution when a first behavior classifier of the at least two behavior classifiers classifies the pilot as having a first behavior and a second behavior classifier of the at least two behavior classifiers classifies the pilot as having a second behavior;

wherein the conflict resolution includes weighting the first behavior classifier and the second behavior classifier based on the current flight context.

2. The system of claim 1, wherein the pilot state includes at least one of a fatigue or a stress of the pilot.

3. The system of claim 1, wherein the avionics information of the aircraft includes traffic alert and collision avoidance information.

4. The system of claim 3, wherein the one or more processors are further configured to receive a pilot interaction with the aircraft; wherein the one or more processors determine the current flight context for the aircraft based on the avionics information, the flight state, and the pilot interaction.

5. The system of claim 4, wherein the pilot interaction includes at least one of a heart rate or an electrocardiogram of the pilot.

6. The system of claim 1, wherein at least one of the at least two anomaly detection classifiers is an unsupervised machine learning algorithm.

7. The system of claim 6, wherein the one or more processors are configured to train the unsupervised machine learning algorithm for each pilot of the aircraft.

8. The system of claim 1, wherein the one or more processors are configured to receive the stream of images, the avionics information of the aircraft, and the flight state of the aircraft; wherein the one or more processors are configured to classify the current flight context for the aircraft based on the avionics information and the flight state.

9. The system of claim 8, wherein the non-transitory memory maintains previous behaviors and previous contexts associated with the previous behaviors; wherein the one or more processors are configured to classify the current flight context for the aircraft based on the avionics information, the flight state, and the previous contexts associated with the previous behaviors.

10. The system of claim 9, wherein the previous behaviors and the previous contexts are associated with the pilot; wherein the one or more processors are further configured to store the behavior of the pilot and the current flight context of the aircraft in the non-transitory memory.

11. The system of claim 1, wherein the non-transitory memory and the one or more processors are housed in a common housing.

* * * * *